United States Patent
Tokarski et al.

(10) Patent No.: US 7,115,347 B2
(45) Date of Patent: *Oct. 3, 2006

(54) AZINE-BASED DIMERIC CHARGE TRANSPORT MATERIALS

(75) Inventors: Zbigniew Tokarski, Woodbury, MN (US); Nusrallah Jubran, St. Paul, MN (US); Vytautas Getautis, Kaunas (LT); Valentas Gaidelis, Vilnius (LT); Maryte Daskeviciene, Jonava (LT); Edmundas Montrimas, Vilnius (LT); Ingrida Paulauskaite, Kaunas (LT); Jonas Sidaravicius, Vilnius (LT)

(73) Assignee: Samsung Electronics Co., LTD, Kyungki-Do (CN)

( * ) Notice: Subject to any disclaimer, the term of this patent is extended or adjusted under 35 U.S.C. 154(b) by 0 days.

This patent is subject to a terminal disclaimer.

(21) Appl. No.: 10/760,039

(22) Filed: Jan. 16, 2004

(65) Prior Publication Data

US 2004/0265717 A1  Dec. 30, 2004

Related U.S. Application Data

(60) Provisional application No. 60/483,726, filed on Jun. 30, 2003.

(51) Int. Cl.
  *G03G 5/047*  (2006.01)
  *C07C 251/00*  (2006.01)
(52) U.S. Cl. .............. 430/58.65; 430/58.35; 430/72; 430/73; 430/74; 399/159; 564/249
(58) Field of Classification Search .......... 430/58.35, 430/58.65, 72, 73, 74; 564/249; 399/159
See application file for complete search history.

(56) References Cited

U.S. PATENT DOCUMENTS

| | | |
|---|---|---|
| 4,297,426 A | 10/1981 | Sakai et al. |
| 4,415,640 A | 11/1983 | Goto et al. |
| 4,420,548 A | 12/1983 | Sakai et al. |
| 4,786,571 A | 11/1988 | Ueda |
| 4,957,838 A | 9/1990 | Aruga et al. |
| 5,128,227 A | 7/1992 | Monbaliu et al. |
| 6,066,426 A | 5/2000 | Mott et al. |
| 6,099,996 A | 8/2000 | Yanus et al. |
| 6,140,004 A | 10/2000 | Mott et al. |
| 6,214,503 B1 | 4/2001 | Gaidelis et al. |
| 6,340,548 B1 | 1/2002 | Jubran et al. |
| 6,350,553 B1 | 2/2002 | Srinivasan |
| 6,670,085 B1 | 12/2003 | Jubran et al. |
| 6,689,523 B1 | 2/2004 | Law et al. |
| 6,696,209 B1 | 2/2004 | Law et al. |
| 2003/0104294 A1 | 6/2003 | Law et al. |
| 2003/0113132 A1 | 6/2003 | Law et al. |
| 2003/0113643 A1 | 6/2003 | Law et al. |
| 2003/0113644 A1 | 6/2003 | Law et al. |
| 2003/0138712 A1 | 7/2003 | Law et al. |
| 2003/0198880 A1 | 10/2003 | Law et al. |
| 2003/0219662 A1 | 11/2003 | Jubran et al. |

FOREIGN PATENT DOCUMENTS

| | | |
|---|---|---|
| JP | 62-116943 | 11/1985 |
| WO | WO 00/63748 | 10/2000 |

OTHER PUBLICATIONS

Diamond, A.S., ed., Handbook of Imaging Materials, Marcel Dekker, Inc., NY (1991), pp. 395-396.*
Donald Bethell et al, "Oligomeric Bis(1,3-Indandiylidene)azine: Preparation, Electrochemical and spectroscopic properties, and implications for the use of polyazines as conducting materials," J. Chem Soc. Perkin Trans. 2, (6) 1081-1086 (1996).

* cited by examiner

*Primary Examiner*—Janis L. Dote
(74) *Attorney, Agent, or Firm*—Patterson, Thuente, Skaar & Christensen, P.A.

(57) ABSTRACT

Improved organophotoreceptor comprises an electrically conductive substrate and a photoconductive element on the electrically conductive substrate, the photoconductive element comprising: (a) a charge transport material having the formula

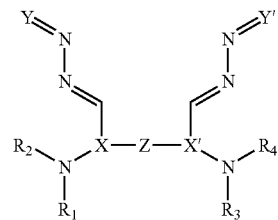

where $R_1$, $R_2$, $R_3$, and $R_4$ comprise, each independently, an alkyl group, an alkenyl group, an aromatic group, a heterocyclic group, or a part of a ring group; X and X' comprise, each independently, an aromatic group; Y and Y' comprise, each independently, a (disubstituted)methylene group; and Z is a linking group; (b) a charge generating compound; and (c) an electrically conductive substrate on which said charge transport material and said charge generating compound are located. Corresponding electrophotographic apparatuses and imaging methods are also described.

21 Claims, No Drawings

AZINE-BASED DIMERIC CHARGE TRANSPORT MATERIALS

CROSS REFERENCE TO RELATED APPLICATION

This application claims priority to now abandoned U.S. Provisional Patent Application Ser. No. 60/483,726 filed Jun. 30, 2003 to Tokarski et al., entitled "Azine-Based Dimeric Charge Transport Materials," incorporated herein by reference.

FIELD OF INVENTION

This invention relates to organophotoreceptors suitable for use in electrophotography and, more specifically, to an organophotoreceptor having charge transport materials comprising at least two azine groups bonded together through a linking group.

BACKGROUND

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas where light strikes the surface, thereby forming a pattern of charged and uncharged areas, referred to as a latent image. A liquid or solid toner is then provided in the vicinity of the latent image, and toner droplets or particles deposit in the vicinity of either the charged or uncharged areas to create a toned image on the surface of the photoconductive layer. The resulting toned image can be transferred to a suitable ultimate or intermediate receiving surface, such as paper, or the photoconductive layer can operate as an ultimate receptor for the image. The imaging process can be repeated many times to complete a single image, for example, by overlaying images of distinct color components or effect shadow images, such as overlaying images of distinct colors to form a full color final image, and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are present in the element in separate layers, each of which can optionally be combined with a polymeric binder, deposited on the electrically conductive substrate. Two arrangements are possible for a two-layer photoconductive element. In one two-layer arrangement (the "dual layer" arrangement), the charge-generating layer is deposited on the electrically conductive substrate and the charge transport layer is deposited on top of the charge generating layer. In an alternate two-layer arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept at least one type of these charge carriers and transport them through the charge transport layer in order to facilitate discharge of a surface charge on the photoconductive element. The charge transport material can be a charge transport compound, an electron transport compound, or a combination of both. When a charge transport compound is used, the charge transport compound accepts the hole carriers and transports them through the layer with the charge transport compound. When an electron transport compound is used, the electron transport compound accepts the electron carriers and transports them through the layer with the electron transport compound.

SUMMARY OF THE INVENTION

In a first aspect, the invention features an organophotoreceptor that includes:

(a) a charge transport material having the formula

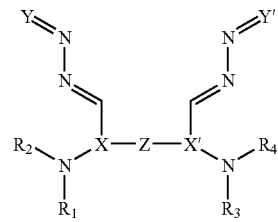

where $R_1$, $R_2$, $R_3$, and $R_4$ comprise, each independently, an alkyl group, an alkenyl group, an aromatic group, a heterocyclic group, or a part of a ring group;

X and X' comprise, each independently, an aromatic group such as, for example, a $C_6H_3$ group;

Y and Y' comprise, each independently, a (disubstituted) methylene group, such as a (di-aromatic)methylene group, for example, 10H-anthracen-9-ylidene group, 9-fluorenylidenyl group, and diarylmethylene group (e.g. diphenylmethylene group); and Z is a linking group, such as $-(CH_2)_m-$ where m is an integer between 1 and 20, inclusive, and one or more of the methylene groups is optionally replaced by O, S, C=O, O=S=O, a heterocyclic group, an aromatic group, urethane, urea, an ester group, an $NR_6$ group, or a $CR_8R_9$ group where $R_6$, $R_8$, and $R_9$ are, independently, H, hydroxyl, thiol, carboxyl, an amino group, an alkyl group, an alkenyl group, a heterocyclic group, an aromatic group, or part of a ring group; and (b) a charge generating compound; and (c) an electrically conductive substrate over which the charge transport material and the charge generating compound are located.

The organophotoreceptor may be provided, for example, in the form of a plate, a belt, a flexible belt, a flexible disk, a sheet, a rigid drum, or a sheet around a rigid or compliant drum. In one embodiment, the organophotoreceptor includes: (a) a photoconductive element comprising the charge transport material, the charge generating compound, a second charge transport material, and a polymeric binder; and (b) the electrically conductive substrate.

In a second aspect, the invention features an electrophotographic imaging apparatus that comprises (a) a light imaging component; and (b) the above-described organophotoreceptor oriented to receive light from the light imaging component. The apparatus can further comprise a toner dispenser. The method of electrophotographic imaging with photoreceptors containing the above noted charge transport materials is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features a charge transport material having the general formula above.

These photoreceptors can be used successfully with both dry and liquid toners to produce high quality images. The production of high quality images can be maintained after repeated cycling.

Other features and advantages of the invention will be apparent from the following description of the preferred embodiments thereof, and from the claims.

DETAILED DESCRIPTION

An organophotoreceptor as described herein has an electrically conductive substrate and a photoconductive element comprising a charge generating compound and a charge transport material having two azine groups, each bonded independently to a (disubstituted)methylene group and an amine substituted aromatic group. The two azine groups are also bonded together by a linking group. These charge transport materials have desirable properties as evidenced by their performance in organophotoreceptors for electrophotography. The organophotoreceptors are particularly useful in laser printers and the like as well as photocopiers, scanners and other electronic devices based on electrophotography. The use of these charge transport materials is described below in the context of laser printers use, although their application in other devices operating by electrophotography can be generalized from the discussion below.

To produce high quality images, particularly after multiple cycles, it is desirable for the charge transport materials to form a homogeneous solution with the polymeric binder and remain approximately homogeneously distributed through the organophotoreceptor material during the cycling of the material. In addition, it is desirable to increase the amount of charge that the charge transport material can accept (indicated by a parameter known as the acceptance voltage or "$V_{acc}$"), and to reduce retention of that charge upon discharge (indicated by a parameter known as the discharge voltage or "$V_{dis}$").

The charge transport materials can be classified as a charge transport compound or an electron transport compound. There are many charge transport compounds and electron transport compounds known in the art for electrophotography. Non-limiting examples of charge transport compounds include, for example, pyrazoline derivatives, fluorene derivatives, oxadiazole derivatives, stilbene derivatives, enamine derivatives, enamine stilbene derivatives, hydrazone derivatives, carbazole hydrazone derivatives, (N,N-disubstituted)arylamines such as triaryl amines, polyvinyl carbazole, polyvinyl pyrene, polyacenaphthylene, or multi-hydrazone compounds comprising at least two hydrazone groups and at least two groups selected from the group consisting of (N,N-disubstituted)arylamine such as triphenylamine and heterocycles such as carbazole, julolidine, phenothiazine, phenazine, phenoxazine, phenoxathiin, thiazole, oxazole, isoxazole, dibenzo(1,4)dioxin, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline.

Non-limiting examples of electron transport compounds include, for example, bromoaniline, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno[1,2-b]thiophene-4-one, and 1,3,7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethylidene) thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene)malononitrile, and diethyl(4-n-butoxycarbonyl-2,7-dinitro-9-fluorenylidene)-malonate, anthraquinodimethane derivatives such as 11,11,12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxy carbonyl) methylene]anthrone, 1,8-dihydroxy-10-[bis(ethoxycarbonyl)methylene] anthrone, and 1-cyano-10-[bis (ethoxycarbonyl)methylene)anthrone, 7-nitro-2-aza-9-fluroenylidene-malononitrile, diphenoquinone derivatives, benzoquinone derivatives, naphtoquinone derivatives, quinine derivatives, tetracyanoethylenecyanoethylene, 2,4,8-trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyano quinoedimethane, 2,4,5,7-tetranitro-9-fluorenone, 2,4,7-trinitro-9-dicyanomethylene fluorenone, 2,4,5,7-tetranitroxanthone derivatives, and 2,4,8-trinitrothioxanthone derivatives. In some embodiments of interest, the electron transport compound comprises an (alkoxycarbonyl-9-fluorenylidene)malononitrile derivative, such as (4-n-butoxycarbonyl-9-fluorenylidene) malononitrile.

Although there are many charge transport materials available, there is a need for other charge transport materials to meet the various requirements of particular electrophotography applications.

In electrophotography applications, a charge-generating compound within an organophotoreceptor absorbs light to form electron-hole pairs. These electrons and holes can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport materials described herein are especially effective at transporting charge, and in particular holes from the electron-hole pairs formed by the charge generating compound. In some embodiments, a specific electron transport compound or charge transport compound can also be used along with the charge transport material of this invention.

The layer or layers of materials containing the charge generating compound and the charge transport materials are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport material can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport material and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport material and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the entire surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

As described herein, an organophotoreceptor comprises a charge transport material having the formula

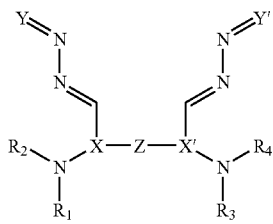

where $R_1$, $R_2$, $R_3$, and $R_4$ comprise, each independently, an alkyl group, an alkenyl group, an aromatic group, a heterocyclic group, or a part of a ring group;

X and X' comprise, each independently, an aromatic group;

Y and Y' comprise, each independently, a (disubstituted) methylene group, such as, a (di-aromatic)methylene group, for example, 10H-anthracen-9-ylidene group, 9-fluorenylidenyl group, and diarylmethylene group (e.g. diphenylmethylene group); and Z is a linking group, such as —$(CH_2)_m$— where m is an integer between 1 and 20, inclusive, and one or more of the methylene groups is optionally replaced by O, S, C=O, O=S=O, a heterocyclic group, an aromatic group, urethane, urea, an ester group, an $NR_6$ group, or a $CR_8R_9$ group where $R_6$, $R_8$, and $R_9$ are, independently, H, hydroxyl, thiol, carboxyl, an amino group, an alkyl group, an alkenyl group, a heterocyclic group, an aromatic group, or part of a ring group.

An aromatic group can be any conjugated ring system containing 4n+2 pi-electrons. There are many criteria available for determining aromaticity. A widely employed criterion for the quantitative assessment of aromaticity is the resonance energy. In some embodiments, the resonance energy of the aromatic group is at least 10 KJ/mol. In further embodiments, the resonance energy of the aromatic group is greater than 0 KJ/mol. Aromatic groups may be classified as an aromatic heterocyclic group which contains at least a heteroatom in the 4n+2 pi-electron ring, or as an aryl group which does not contain a heteroatom in the 4n+2 pi-electron ring. The aromatic group may comprise a combination of aromatic heterocyclic group and aryl group. Nonetheless, either the aromatic heterocyclic or the aryl group may have at least one heteroatom in a substituent attached to the 4n+2 pi-electron ring. Furthermore, either the aromatic heterocyclic or the aryl group may comprise a monocyclic or polycyclic (such as bicyclic, tricyclic, etc.) ring.

Non-limiting examples of the aromatic heterocyclic group are furanyl, thiophenyl, pyrrolyl, indolyl, carbazolyl, benzofuranyl, benzothiophenyl, dibenzofuranyl, dibenzothiophenyl, pyridinyl, pyridazinyl, pyrimidinyl, pyrazinyl, triazinyl, tetrazinyl, petazinyl, quinolinyl, isoquinolinyl, cinnolinyl, phthalazinyl, quinazolinyl, quinoxalinyl, naphthyridinyl, pteridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, thianthrenyl, and a combination thereof. The aromatic heterocyclic group may also include any combination of the above aromatic heterocyclic groups bonded together either by a bond (as in bicarbazolyl) or by a linking group (as in 1,6-di(10H-10-phenothiazinyl)hexane). The linking group may include an aliphatic group, an aromatic group, a heterocyclic group, or a combination thereof. Furthermore, either an aliphatic group or an aromatic group within a linking group may comprise at least one heteroatom such as O, S, and N.

Non-limiting examples of the aryl group are phenyl, naphthyl, benzyl, or tolanyl group, sexiphenylene, phenanthrenyl, anthracenyl, coronenyl, and tolanylphenyl. The aryl group may also include any combination of the above aryl groups bonded together either by a bond (as in biphenyl group) or by a linking group (as in stilbenyl, diphenyl sulfone, an arylamine group). The linking group may include an aliphatic group, an aromatic group, a heterocyclic group, or a combination thereof. Furthermore, either an aliphatic group or an aromatic group within a linking group may comprise at least one heteroatom such as O, S, and N. As another example of a (disubstituted)methylene group, a 9-fluorenylidenyl group has the following central nucleus of the formula:

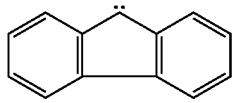

Similarly, a 10H-anthracen-9-ylidene group has the following central nucleus of the formula:

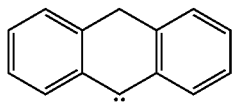

Substitution is liberally allowed on the chemical groups to affect various physical effects on the properties of the compounds, such as mobility, sensitivity, solubility, stability, and the like, as is known generally in the art. In the description of chemical substituents, there are certain practices common to the art that are reflected in the use of language. The term group indicates that the generically recited chemical entity (e.g., alkyl group, phenyl group, aromatic group, heterocyclic group, (disubstituted)methylene group, 9-fluorenylidenyl group, 10H-anthracen-9-ylidene group, diarylmethylene group, etc.) may have any substituent thereon which is consistent with the bond structure of that group. For example, where the term 'alkyl group' is used, that term would not only include unsubstituted linear, branched and cyclic alkyls, such as methyl, ethyl, isopropyl, tert-butyl, cyclohexyl, dodecyl and the like, but also substituents having heteroatom such as 3-ethoxylpropyl, 4-(N-ethylamino)butyl, 3-hydroxypentyl, 2-thiolhexyl, 1,2,3-tribromopropyl, and the like. However, as is consistent with such nomenclature, no substitution would be included within the term that would alter the fundamental bond structure of the underlying group. For example, where a phenyl group is recited, substitution such as 1-aminophenyl, 2,4-dihydroxyphenyl, 1,3,5-trithiophenyl, 1,3,5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form. Where the term a "central nucleus of the formula" is used and a structural formula is shown, any substituent may be provided on that formula, as long as the substitution does not alter the underlying bond structure of the formula (e.g., by require a double bond to be converted to a single bond, or opening a ring group, or dropping a described substituent group in the formula). Where the term moiety is used, such as alkyl moiety or phenyl moiety, that terminology indicates that the chemical material is not substituted. Where the term alkyl moiety is used, that term represents only an unsubstituted alkyl hydrocarbon group, whether branched, straight chain, or cyclic.

The charge transport material may or may not be symmetrical. Thus, for example, Y and Y' may be the same or different; X and X' may be the same or different; and $R_1$, $R_2$, $R_3$, and $R_4$ may be the same or different. In addition, the above-described formula for the charge transport material is intended to cover isomers.

Organophotoreceptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport material and a charge generating compound in a polymeric binder, which may or may not be in the same layer, as well as a second charge transport material such as a charge transport compound or an electron transport compound in some embodiments. For example, the charge transport material and the charge generating compound can be in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester (e.g., polyethylene terephthalate or polyethylene naphthalate), polyimide, polysulfone, polypropylene, nylon, polyester, polycarbonate, polyvinyl resin, polyvinyl fluoride, polystyrene and the like. Specific examples of polymers for supporting substrates included, for example, polyethersulfone (STABAR™ S-100, available from ICI), polyvinyl fluoride (TEDLAR™, available from E.I. DuPont de Nemours & Company), polybisphenol-A polycarbonate (MAKROFOL™, available from Mobay Chemical Company) and amorphous polyethylene terephthalate (MELINAR™, available from ICI Americas, Inc.). The electrically conductive materials may be graphite, dispersed carbon black, iodine, conductive polymers such as polypyrroles and CALGON® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material that is capable of absorbing light to generate charge carriers, such as a dye or pigment. Non-limiting examples of suitable charge generating compounds include, for example, metal-free phthalocyanines (e.g., ELA 8034 metal-free phthalocyanine available from H.W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygallium phthalocyanine, squarylium dyes and pigments, hydroxy-substituted squarylium pigments, perylimides, polynuclear quinones available from Allied Chemical Corporation under the trade name INDOFAST™ Double Scarlet, INDOFAST™ Violet Lake B, INDOFAST™ Brilliant Scarlet and INDOFAST™ Orange, quinacridones available from DuPont under the trade name MONASTRAL™ Red, MONASTRAL™ Violet and MONASTRAL™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may optionally contain a second charge transport material which may be a charge transport compound, an electron transport compound, or a combination of both. Generally, any charge transport compound or electron transport compound known in the art can be used as the second charge transport material, such as the charge transport compounds and electron transport compounds described above.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the UV stabilizers may not be their UV stabilizing abilities, although the UV stabilizing ability may be further advantageous in reducing degradation of the organophotoreceptor over time. The improved synergistic performance of organophotoreceptors with layers comprising both an electron transport compound and a UV stabilizer are described further in copending U.S. patent application Ser. No. 10/425,333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as TINUVIN™ 144 and TINUVIN™ 292 (from Ciba Specialty Chemicals, Terrytown, N.Y.), hindered alkoxydialkylamines such as TINUVIN™ 123 (from Ciba Specialty Chemicals), benzotriazoles such as TINUVIN™ 328, TINUVIN™ 900 and TINUVIN™ 928 (from Ciba Specialty Chemicals), benzophenones such as SANDUVOR™ 3041 (from Clariant Corp., Charlotte, N.C.), nickel compounds such as Arbestab (from Robinson Brothers Ltd, West Midlands, Great Britain), salicylates, cyanocinnamates, benzylidene malonates, benzoates, oxanilides such as SANDUVOR™ VSU (from Clariant Corp., Charlotte, N.C.), triazines such as Cyagard UV-1164 (from Cytec Industries Inc., N.J.), polymeric sterically hindered amines such as Luchem (from Atochem North America, Buffalo, N.Y.). In some embodiments, the light stabilizer is selected from the group consisting of hindered trialkylamines having the following formula:

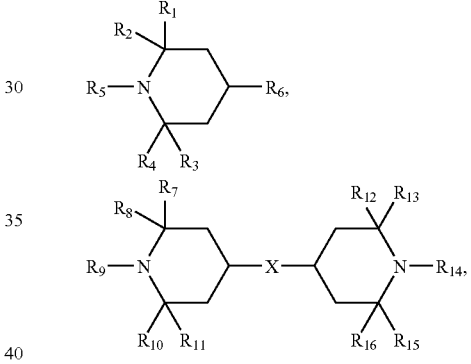

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, independently, hydrogen, alkyl group, or ester, or ether group; and $R_5$, $R_9$, and $R_{14}$ are, independently, alkyl group; and X is a linking group selected from the group consisting.

The binder generally is capable of dispersing or dissolving the charge transport material (in the case of the charge transport layer or a single layer construction), the charge generating compound (in the case of the charge generating layer or a single layer construction) and/or an electron transport compound for appropriate embodiments. Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether)-co-dicyclopentadiene, copolymers of monomers used in the above-mentioned polymers, and combinations thereof. Specific suitable binders include, for example, polyvinyl butyral, polycarbonate, and polyester. Non-limiting examples of polyvinyl butyral include BX-1 and BX-5 from Sekisui Chemical Co. Ltd., Japan. Non-limiting examples of suitable polycarbonate include polycarbonate A which is derived from bisphenol-A (e.g. Iupilon-A from Mitsubishi Engineering Plastics, or Lexan 145 from General Electric); polycarbonate Z which is derived from cyclohexylidene bisphenol (e.g. Iupilon-Z from Mitsubishi Engineering Plastics Corp, White Plain, N.Y.); and polycarbonate C which is derived from methyl-bisphenol A (from Mitsubishi Chemical Corporation). Non-limiting examples of suitable polyester binders include ortho-polyethylene terephthalate (e.g. OPET TR-4 from Kanebo Ltd., Yamaguchi, Japan).

Suitable optional additives for any one or more of the layers include, for example, antioxidants, coupling agents, dispersing agents, curing agents, surfactants, and combinations thereof.

The photoconductive element overall typically has a thickness from about 10 microns to about 45 microns. In the dual layer embodiments having a separate charge generating layer and a separate charge transport layer, charge generation layer generally has a thickness form about 0.5 microns to about 2 microns, and the charge transport layer has a thickness from about 5 microns to about 35 microns. In embodiments in which the charge transport material and the charge generating compound are in the same layer, the layer with the charge generating compound and the charge transport composition generally has a thickness from about 7 microns to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent, in further embodiments in an amount from about 1 to about 15 weight percent, and in other embodiments in an amount from about 2 to about 10 weight percent, based on the weight of the photoconductive layer. The charge transport material is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional second charge transport material, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional charge transport material in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of binder concentrations for the dual layer embodiments within the explicit ranges above are contemplated and are within the present disclosure.

For the embodiments with a single layer having a charge generating compound and a charge transport material, the photoconductive layer generally comprises a binder, a charge transport material, and a charge generation compound. The charge generation compound can be in an amount from about 0.05 to about 25 weight percent and in further embodiment in an amount from about 2 to about 15 weight percent, based on the weight of the photoconductive layer. The charge transport material can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optional additives, such as any conventional additives. A single layer with a charge transport composition and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport material may comprise a second charge transport material. The optional second charge transport material, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport layer can advantageously further include a UV light stabilizer. In particular, the electron transport layer generally can comprise an electron transport compound, a binder, and an optional UV light stabilizer. An overcoat layer comprising an electron transport compound is described further in copending U.S. patent application Ser. No. 10/396,536, U.S. Pat. No. 6,890,693, to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any one or more appropriate layers of the photoconductor generally is in an amount from about 0.5 to about 25 weight percent and in some embodiments in an amount from about 1 to about 10 weight percent, based on the weight of the particular layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, the charge transport material of this invention, a second charge transport material such as a charge transport compound or an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer or a protective layer may form the uppermost layer of the photoconductor element. A barrier layer may be sandwiched between the release layer and the photoconductive element or used to overcoat the photoconductive element. The barrier layer provides protection from abrasion and/or carrier liquid to the underlayers. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

An overcoat layer may comprise an electron transport compound as described further in copending U.S. patent application Ser. No. 10/396,536, filed on Mar. 25, 2003 U.S. Pat. No. 6,890,693, to Zhu et al. entitled, "Organoreceptor With An Electron Transport Layer," incorporated herein by reference. For example, an electron transport compound, as described above, may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrrolidone, polyurethane, polymethyl methacrylate, poly(hydroxy amino ether) and the like. Barrier and adhesive layers are described further in U.S. Pat. No. 6,180,305 to Ackley et al., entitled "Organic Photoreceptors for Liquid Electrophotography," incorporated herein by reference.

Sub-layers can comprise, for example, polyvinylbutyral, organosilanes, hydrolyzable silanes, epoxy resins, polyesters, polyamides, polyurethanes, methylcellulose and the like. In some embodiments, the sub-layer has a dry thickness between about 20 Angstroms and about 2,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport materials as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. Patent Applications 2002/0128349, entitled "Liquid Inks Comprising A Stable Organosol," and 2002/0086916, entitled "Liquid Inks Comprising Treated Colorant Particles," and U.S. Pat. No. 6,649,316, entitled "Phase Change Developer For Liquid Electrophotography," all three of which are incorporated herein by reference.

Charge Transport Material

In some embodiments, the organophotoreceptors as described herein can comprise an improved charge transport material with two azine groups. Specifically, the compounds are based on a formula

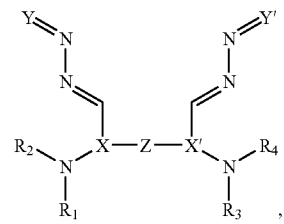

(1)

where $R_1$, $R_2$, $R_3$, and $R_4$ comprise, each independently, an alkyl group, an alkenyl group, an aromatic group, a heterocyclic group, or a part of a ring group;

X and X' comprise, each independently, an aromatic group;

Y and Y' comprise, each independently, a (disubstituted) methylene group, such as a (di-aromatic)methylene group, for example, 10H-anthracen-9-ylidene group, 9-fluorenylidenyl group, and diarylmethylene group (e.g. diphenylmethylene group); and Z is a linking group, such as —$(CH_2)_m$— where m is an integer between 1 and 20, inclusive, and one or more of the methylene groups is optionally replaced by O, S, C=O, O=S=O, a heterocyclic group, an aromatic group, urethane, urea, an ester group, an $NR_6$ group, or a $CR_8R_9$ group where $R_6$, $R_8$, and $R_9$ are, independently, H, hydroxyl, thiol, carboxyl, an amino group, an alkyl group, an alkenyl group, a heterocyclic group, an aromatic group, or part of a ring group.

Non-limiting examples of such charge transport materials have the following formulas:

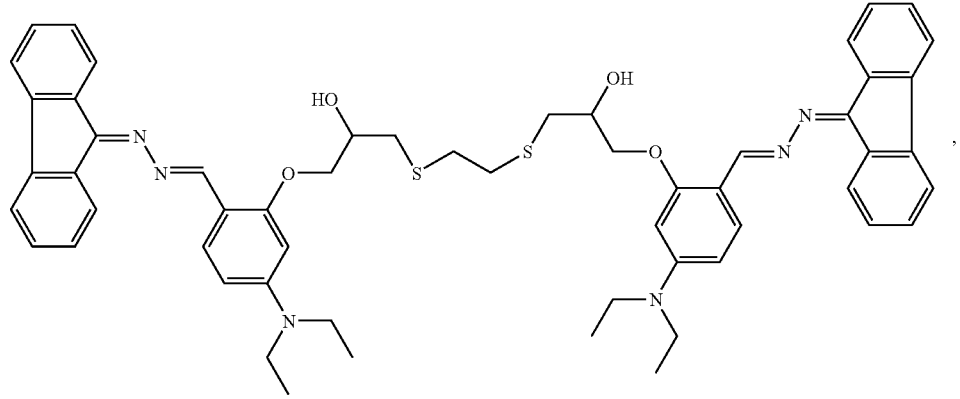

(2)

-continued
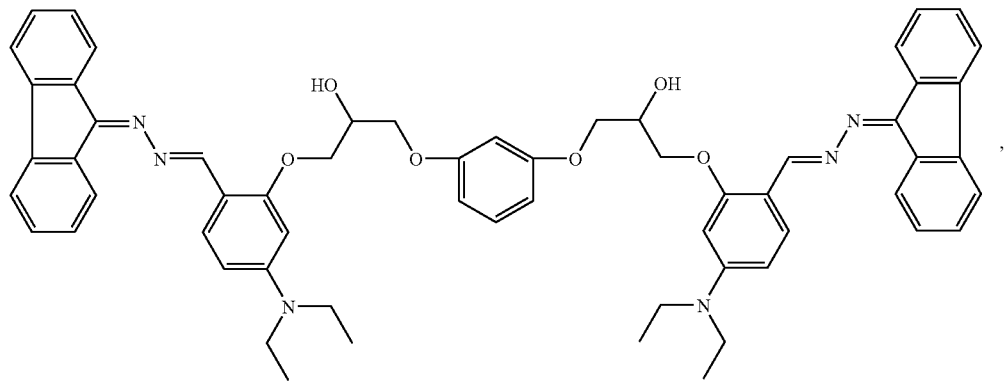
(3)
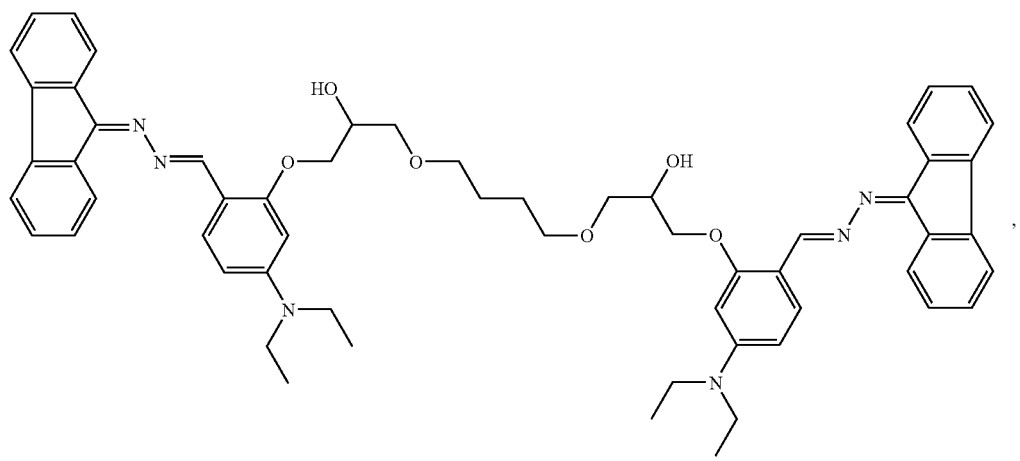
(4)
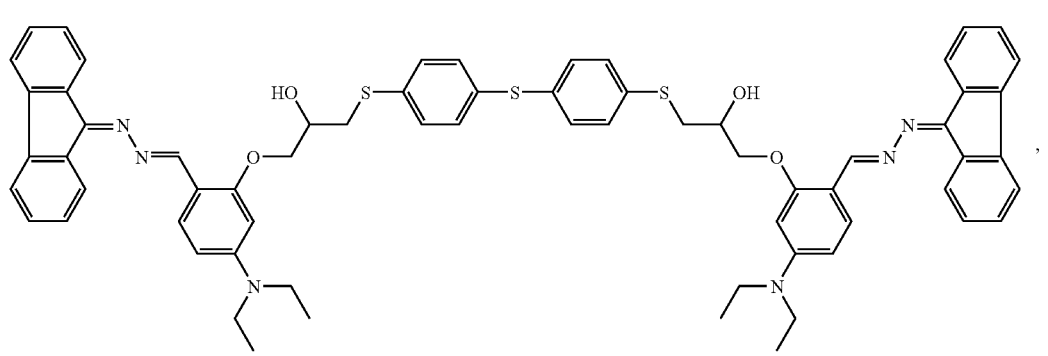
(5)
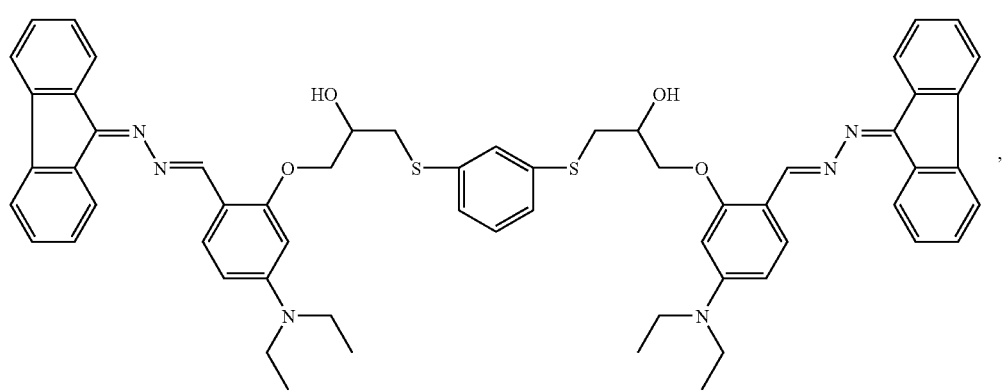
(6)

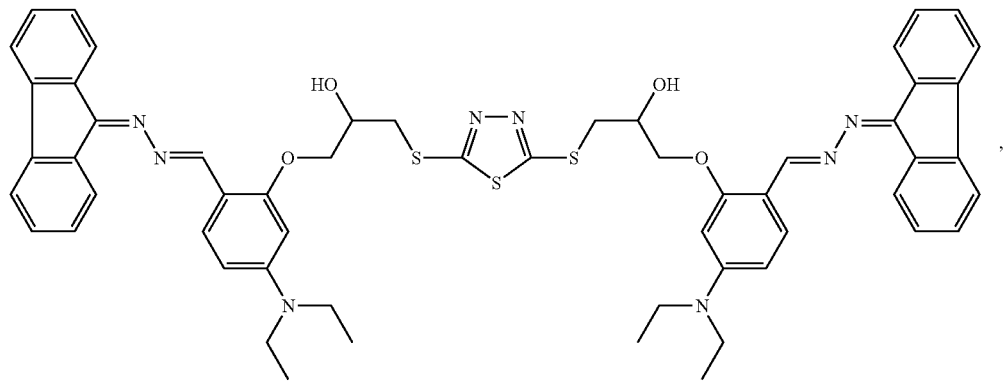
(7)
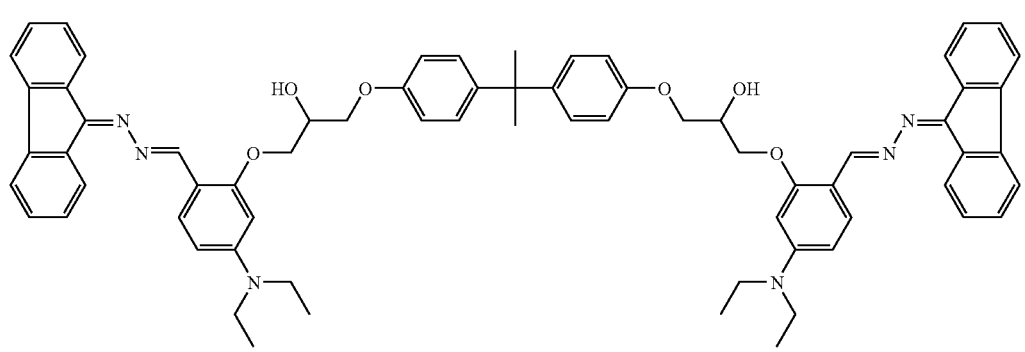
(8)
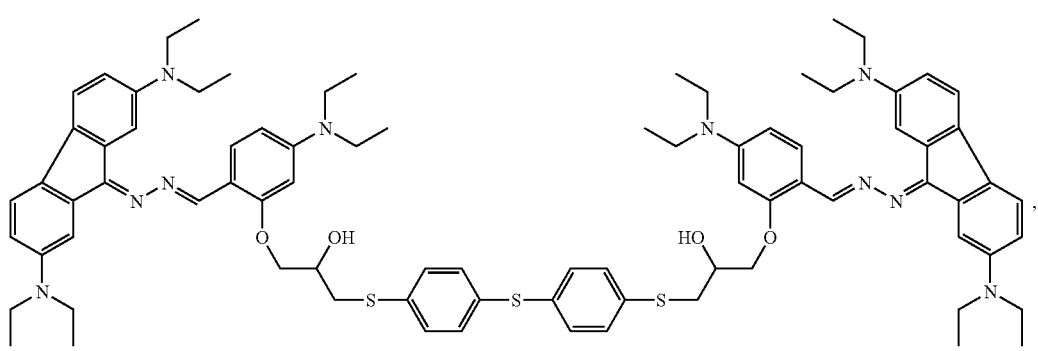
(9)
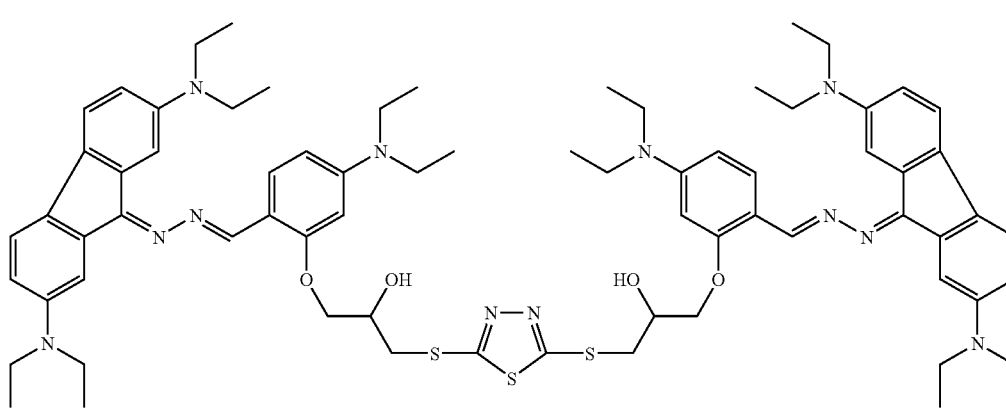
(10)
and

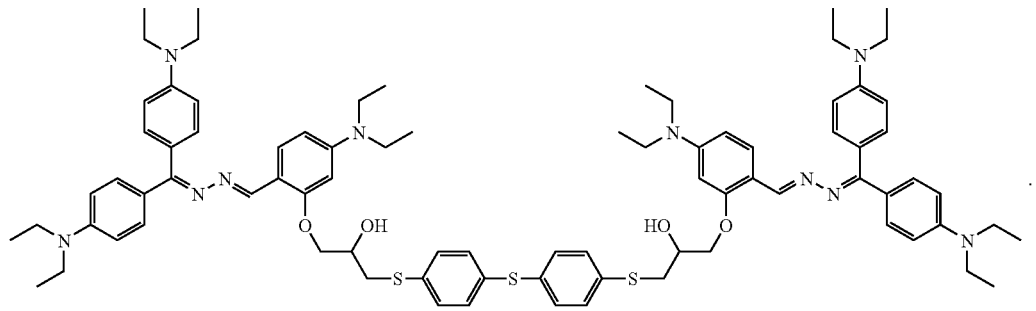

(11)

These photoreceptors may be used successfully with both dry toners and liquid toners to produce high quality images. The high quality of the images can be maintained after repeated cycling.

Synthesis of Charge Transport Materials

The synthesis of the charge transport materials of this invention can be prepared by the following multi-step synthetic procedures, although other suitable procedures can be used by a person of ordinary skill in the art based on the disclosure herein.

The first step is the reaction of a (disubstituted)ketone, such as diphenyl ketone, 9-fluorenone, and 10H-anthracenone, with an excess of hydrazine to form the corresponding (disubstituted)ketone hydrazone. In the second step, the (disubstituted)ketone hydrazone reacts with an aromatic aldehyde having a (disubstituted)amine group and a hydroxyl group to form the corresponding azine compound having a (disubstituted)amine group and a hydroxyl group. This step supplies the Y, X, $R_1$ and $R_2$ groups or the Y', X', $R_3$ and $R_4$ groups of formula (1).

In the third step, the azine compound having a (disubstituted)amine group and a hydroxyl group reacts with an organic halide comprising an epoxy group in the presence of an alkaline to form the corresponding azine compound having a (disubstituted)amine group and an epoxy group. Non-limiting examples of suitable organic halide comprising an epoxy group for this invention are epihalohydrins, such as epichlorohydrin. The organic halide comprising an epoxy group may also be prepared by the epoxidation reaction of the corresponding organic halide having an olefin group. The epoxidation reaction is described in Carey et al., "Advanced Organic Chemistry, Part B: Reactions and Synthesis," New York, 1983, pp. 494–498, incorporated herein by reference. The organic halide having an olefin group may be prepared by the Wittig reaction between a suitable organic halide having an aldehyde or keto group and a suitable Wittig reagent. The Wittig and related reactions are described in Carey et al., "Advanced Organic Chemistry, Part B: Reactions and Synthesis," New York, 1983, pp. 69–77, incorporated herein by reference. This step forms a reactive functional group that becomes a portion of the linking group Z.

The next step is the dimerization of the azine compound having a (disubstituted)amine group and an epoxy group with a linker in the presence of triethylamine. The linker has two functional groups that are reactive towards epoxy group. The linker may be a diol, a dithiol, a diamine, a dicarboxlyic acid, a hydroxylamine, an amino acid, a hydroxyl acid, a thiol acid, a hydroxythiol, or a thioamine. Non-limiting examples of suitable dithiol are 4,4'-thiobisbenzenethiol, 1,4-benzenedithiol, 1,3-benzenedithiol, sulfonyl-bis(benzenethiol), 2,5-dimecapto-1,3,4-thiadiazole, 1,2-ethanedithiol, 1,3-propanedithiol, 1,4-butanedithiol, 1,5-pentanedithiol, and 1,6-hexanedithiol. Non-limiting examples of suitable diols are 2,2'-bi-7-naphtol, 1,4-dihydroxybenzene, 1,3-dihydroxybenzene, 10,10-bis(4-hydroxyphenyl)anthrone, 4,4'-sulfonyldiphenol, bisphenol, 4,4'-(9-fluorenylidene)diphenol, 1,10-decanediol, 1,5-pentanediol, diethylene glycol, 4,4'-(9-fluorenylidene)-bis(2-phenoxyethanol), bis(2-hydroxyethyl) terephthalate, bis[4-(2-hydroxyethoxy)phenyl] sulfone, hydroquinone-bis (2-hydroxyethyl)ether, and bis(2-hydroxyethyl) piperazine. Non-limiting examples of suitable diamine are diaminoarenes, and diaminoalkanes. Non-limiting examples of suitable dicarboxylic acid are phthalic acid, terephthalic acid, adipic acid, and 4,4'-biphenyldicarboxylic acid. Non-limiting examples of suitable hydroxylamine are p-aminophenol and fluoresceinamine. Non-limiting examples of suitable amino acid are 4-aminobutyric acid, phenylalanine, and 4-aminobenzoic acid. Non-limiting examples of suitable hydroxyl acid are salicylic acid, 4-hydroxybutyric acid, and 4-hydroxybenzoic acid. Non-limiting examples of suitable hydroxythiol are monothiohydroquinone and 4-mercapto-1-butanol. Non-limiting example of suitable thioamine is p-aminobenzenethiol. Non-limiting example of suitable thiol acid are 4-mercaptobenzoic acid and 4-mercaptobutyric acid. Almost all of the above di-functional compounds are available commercially from Aldrich and other chemical suppliers.

Symmetrical charge transport materials may be prepared by reacting an azine compound having a (disubstituted) amine group and an epoxy group with a symmetrical linker in a ratio of 2:1. Unsymmetrical charge transport materials may be prepared by using an unsymmetrical linker, such as hydroxylamine compounds, hydroxythiol compounds, and thioamine compounds. Alternatively, unsymmetrical charge transport materials may be prepared by reacting two different azine compounds having a (disubstituted)amine group and an epoxy group with either a symmetrical or an unsymmetrical linker. The reaction conditions can be selected to favor the formation of the asymmetric compound in a sequential or simultaneous reaction. While a mixture of symmetric and asymmetric compounds may be formed, these compounds generally may be separated from each other using available techniques such as thin layer chromatography or column chromatography. Similarly, either a symmetrical or unsymmetrical compound can be formed by reacting a hydroxyl substituted azine from step two with an epoxy substituted azine from step 3 in which the hydroxyl directly bonds with the epoxy group.

The invention will now be described further by way of the following examples.

EXAMPLES

Example 1

Synthesis and Characterization Charge Transport Materials

This example described the synthesis and characterization of Compounds (2)–(11) in which the numbers refer to formula numbers above. The characterization involves both chemical characterization and the electronic characterization of materials formed with the compound.

9-Fluorenone Hydrazone

9-Fluorenone (200 g, 1.1 mol, from Aldrich, Milwaukee, Wis.) and hydrazine monohydrate (160 ml, 3.3 mol, from Aldrich, Milwaukee, Wis.) were dissolved in 1000 ml of 2-propanol in a 2000 ml 2-neck round bottom flask equipped with a reflux condenser and a mechanical stirrer. Concentrated hydrochloric acid (4 ml) was then added, and the mixture was refluxed for one hour. The mixture was cooled slowly to room temperature, and the crude solid product was harvested by filtration. The solid was washed with isopropanol and then recrystallized from dioxane to obtain 150 g (74% yield) of 9-fluorenone hydrazone.

4-Diethylaminosalicylaldehyde 9-Fluorenone Azine

9-Fluorenone hydrazone (50.4 g, 0.26 mol) and 4-diethylaminosalicylaldehyde (50 g, 0.26 mol, from Aldrich, Milwaukee, Wis.) were dissolved in 100 ml of dioxane in a 250 ml round bottom flask equipped with a reflux condenser. The mixture was refluxed for 2 hours. At the end of the reaction, the dioxane was evaporated to give an oily residue that was dissolved in 2-propanol. The solution was cooled to 5° C. The crystals that formed upon standing were filtered off, washed with 2-propanol, and recrystallized from a mixture of toluene and 2-propanol in a ratio of 1:2 by volume to yield 81 g (85%) of 4-diethylaminosalicylaldehyde 9-fluorenone azine. The melting point was found to be 209–211° C. The $^1$H NMR spectrum (100 MHz) of the product in CDCl$_3$ was characterized by the following chemical shifts ($\delta$, ppm): 11.8 (s, 1H, OH); 8.5 (s, 1H, CH=N); 8.3–7.0 (m, 9H, Ar); 6.3 (m, 2H, 3-H, 6-H of 1,2,4-subst. Ph); 3.3 (q, J=7.4 Hz, 4H, CH$_2$); and 1.2 (t, J=7.2 Hz, 6H, CH$_3$). An elemental analysis yielded the following results in weight percent: C, 77.98; H, 6.15; N, 11.25, which compared with the following calculated values for C$_{24}$H$_{23}$N$_3$O in weight percent: C, 78.02; H, 6.27; N, 11.37.

Glycidyl Ether of 4-Diethylaminosalicylaldehyde 9-Fluorenone Azine

Epichlorohydrin (160 ml, 2 mol, from Aldrich, Milwaukee, Wis.) and 4-diethylaminosalicylaldehyde 9-fluorenone azine (50 g, 0.14 mol, prepared as described above) were added to a 250 ml 3-neck round bottom flask equipped with a reflux condenser, a thermometer, and a mechanical stirrer. The reaction mixture was stirred vigorously at 35–40° C. for 7 hours. During this time, 26.8 g (0.4 mol) of powdered 85% potassium hydroxide and 6.8 g (0.05 mol) of anhydrous sodium sulfate (Na$_2$SO$_4$) were added in three portions with prior cooling of the reaction mixture to 20–25° C. After the termination of the reaction, the mixture was cooled to room temperature, and the unreacted solids were filtered off. The filtrate was extracted with diethyl ether and washed with distilled water until the washed water had a neutral pH. The organic layer was dried over anhydrous magnesium sulfate, treated with activated charcoal, and filtered. The solvents were removed and the residue was subjected to column chromatography (silica gel, grade 62, 60–200 mesh, 150 Å, Aldrich) using a mixture of acetone and hexane in a ratio of 1:4 by volume as the eluant. Fractions containing the product were collected, and the solvents were evaporated to yield an oily residue that was crystallized from a mixture of acetone and 2-propanol in a ratio of 3:1 by volume. The crystals were filtered off and washed with 2-propanol to yield 35 g (65%) of glycidyl ether of 4-diethylaminosalicylaldehyde 9-fluorenone azine. The melting point was found to be 135.5–136.6° C. The $^1$H NMR spectrum (100 MHz) of the product in CDCl$_3$ was characterized by the following chemical shifts ($\delta$, ppm): 9.1 (s, 1H, CH=N); 8.8 (m, 1H, Ar); 8.2 (d, 1H, 6-H of 1,2,4-subst. Ph); 8.1–7.2 (m, 7H, Ar); 6.5 (d, 1H, 5-H of 1,2,4-subst. Ph); 6.2 (s, 1H, 3-H of 1,2,4-subst. Ph); 4.5–4.2 (dd, 1H, one of OCH$_2$); 4.2–4.0 (dd, 1H, one of OCH$_2$); 3.6–3.3 (m, 5H, CH$_2$N, CH); 3.0 (m, 1H, one of CH$_2$ of oxirane); 2.8 (dd, 1H, one of CH$_2$ of oxirane); and 1.2 (t, 6H, CH$_3$). An elemental analysis yielded the following results in weight percent: C, 76.08; H, 6.31; N, 9.77, which compared with calculated values for C$_{27}$H$_{27}$N$_3$O$_2$ in weight percent: C, 76.21; H, 6.40; N, 9.87.

Compound (2)

Glycidyl ether of 4-diethylaminosalicylaldehyde 9-fluorenone azine (4.5 g, 10.58 mmol) and 1,2-ethanedithiol (0.43 ml, 5.16 mmol, commercially obtained from Aldrich, Milwaukee, Wis.) were dissolved in 10 ml of 2-butanone. Triethylamine (TEA, 0.59 ml, 4.23 mmol, commercially available from Aldrich, Milwaukee, Wis.) was then added and the mixture was refluxed until the 1,2-ethanedithiol and its monosubstituted derivative disappeared (2 hours). The solvent was evaporated and the residue was subjected to column chromatography (silica gel, grade 62, 60–200 mesh, 150 Å, Aldrich) using a mixture of acetone and hexane in a ratio of 1:4 by volume as the eluant. Fractions containing the product were collected and the solvent was evaporated to from an oily residue. The oily residue was dissolved in toluene to form a 20% solid solution that was then poured with intensive stirring into a tenfold excess of n-hexane to yield 3.7 g (76%) of Compound (2). The $^1$H NMR spectrum (100 MHz) of the product in DMSO-d$_6$ was characterized by the following chemical shifts ($\delta$, ppm): 8.9 (s, 2H, CH=N); 8.65 (d, 2H, Ar); 8.2–7.2 (m, 16H, Ar); 6.5 (d, 2H, 5-H of 1,2,4-subst. Ph); 6.2 (s, 2H, 3-H of 1,2,4-subst. Ph); 5.45 (d, 2H, OH); 4.25–3.9 (m, 6H, OCH$_2$CH); 3.45 (q, 8H, CH$_2$CH$_3$); 2.8 (m, 8H, CH$_2$SCH$_2$); and 1.1 (t, 12H, CH$_3$). An elemental analysis yielded the following results in weight percent: C, 70.84; H, 6.28; N, 9.76, which compared with the following calculated values for C$_{56}$H$_{60}$N$_6$S$_2$O$_4$ in weight percent: C, 71.16; H, 6.40; N, 8.89.

Compound (3)

Glycidyl ether of 4-diethylaminosalicylaldehyde 9-fluorenone azine (5 g, 11.75 mmol, prepared previously) and 1,3-benzenediol (0.616 g, 5.6 mmol, from Aldrich, Milwaukee, Wis.) were dissolved in 10 ml of 2-butanone. Triethylamine (0.65 ml, 4.7 mmol) was then added, and the mixture was refluxed for 15 hours. After the evaporation of the solvent, the residue was subjected to column chromatography (silica gel, grade 62, 60–200 mesh, 150 Å, Aldrich) using a mixture of acetone and hexane in a ratio of 1:4 by volume as the eluant. Fractions containing the product were collected, and the solvent was evaporated to from an oily residue. The oily residue was dissolved in toluene to form a 20 wt % solution that was then poured with intensive stirring into a tenfold excess of n-hexane to yield 4.2 g (78%) of Compound (3). The $^1$H NMR spectrum (100 MHz) of the product in CDCl$_3$ was characterized by the following chemical shifts (δ, ppm): 9.0 (s, 2H, CH=N); 8.75 (m, 2H, Ar); 8.2–7.0 (m, 16H, Ar); 6.8–6.05 (m, 7H, Ar); 4.6–4.05 (m, 10H, CH$_2$CHCH$_2$); 3.6–3.1 (m, 10H, OH, CH$_2$CH$_3$); and 1.2 (t, 12H, CH$_3$). An elemental analysis yielded the following results in weight percent: C, 74.84; H, 6.18; N, 9.86, which compared with the following calculated values for C$_{60}$H$_{60}$N$_6$O$_6$ in weight percent: C, 74.98; H, 6.29; N, 9.99.

Compound (4)

4-Diethylaminosalicylaldehyde 9-fluorenone azine (6.04 g, 16.3 mmol), 1,4-butanediol diglycidyl ether (1.50 g, 7.4 mmol, from Aldrich, Milwaukee, Wis.) and 2 ml of triethylamine were dissolved in 10 ml of methyl ethyl ketone. The mixture was refluxed for 45 hours. After the evaporation of the solvent, the residue was subjected to column chromatography (silica gel, grade 62, 60–200 mesh, 150 Å, Aldrich) using a mixture of acetone and hexane in a ratio of 1:4 by volume as the eluant. Fractions containing the product were collected, and the solvent was evaporated to from an oily residue. The oily residue was dissolved in toluene to form a 20 wt % solution, which was then poured with intensive stirring into a tenfold excess of n-hexane to yield 3.8 g (54%) of Compound (4). The $^1$H NMR spectrum (100 MHz) of the product in CDCl$_3$ was characterized by the following chemical shifts (δ, ppm): 8.9 (s, 2H, CH=N); 8.7 (d, 2H, Ar); 8.2–7.1 (m, 16H, Ar); 6.45 (d, 2H, 5-H of 1,2,4-subst. Ph); 6.1 (s, 2H, 3-H of 1,2,4-subst. Ph); 4.1 (m, 6H, OCH$_2$CH); 3.85–3.2 (m, 16H, NCH$_2$CH$_3$, CH$_2$OCH$_2$); 3.0 (s (br), 2H, OH); 1.65 (m, 4H, OCH$_2$(CH$_2$)$_2$CH$_2$O); and 1.2 (t, 12H, CH$_3$). An elemental analysis yielded the following results in weight percent: C, 73.95; H, 6.82; N, 8.87, which compared with the following calculated values for C$_{58}$H$_{64}$N$_6$O$_6$ in weight percent: C, 74.02; H, 6.85; N, 8.93.

Compound (5)

Triethylamine (0.65 ml, 4.7 mmol) was added slowly to a solution of glycidyl ether of 4-diethylaminosalicylaldehyde 9-fluorenone azine (5 g, 11.75 mmol) and 4,4'-thiobisbenzenethiol (1.44 g, 5.73 mmol) in 10 ml of 2-butanone, while the temperature of the reaction mixture was maintained below 30° C. The reaction mixture was stored over night at room temperature. After the evaporation of the solvent, the residue was subjected to column chromatography (silica gel, grade 62, 60–200 mesh, 150 Å, Aldrich) using a mixture of acetone and hexane in a ratio of 1:4 by volume as the eluant. Fractions containing the product were collected, and the solvent was evaporated to from an oily residue. The oily residue was dissolved in toluene to form a 20 wt % product solution, which was then poured with intensive stirring into a tenfold excess of n-hexane to yield 5.1 g (81%) of Compound (5). The $^1$H NMR spectrum (100 MHz) of the product in CDCl$_3$ was characterized by the following chemical shifts (δ, ppm): 8.9 (s, 2H, CH=N); 8.7 (m, 2H, Ar); 8.2–7.1 (m, 22H, Ar); 6.45 (d, 2H, 5-H of 1,2,4-subst. Ph); 6.1 (s, 2H, 3-H of 1,2,4-subst. Ph); 4.4–4.05 (m, 6H, OCH$_2$CH); 3.6–3.0 (m, 12H, SCH$_2$, OH, CH$_2$CH$_3$); and 1.2 (t, 12H, CH$_3$). An elemental analysis yielded the following results in weight percent: C, 71.84; H, 5.59; N, 7.57, which compared with the following calculated values for C$_{66}$H$_{64}$N$_6$S$_3$O$_4$ in weight percent: C, 71.97; H, 5.86; N, 7.63.

Compound (6)

Compound (6) was obtained by a similar procedure for Compound (5) except that 1,3-benzenedithiol (0.815 g, 5.73 mmol) replaced 4,4'-thiobisbenzenethiol (1.44 g, 5.73 mmol). The yield of Compound (6) was 4.6 g (81%). The $^1$H NMR spectrum (100 MHz) of the product in CDCl$_3$ was characterized by the following chemical shifts (δ, ppm): 8.9 (s, 2H, CH=N); 8.75 (m, 2H, Ar); 8.2–7.1 (m, 20H, Ar); 6.45 (d, 2H, 5-H of 1,2,4-subst. Ph); 6.1 (s, 2H, 3-H of 1,2,4-subst. Ph); 4.5–4.0 (m, 6H, OCH$_2$CH); 3.65–3.1 (m, 14H, CH$_2$S, OH, CH$_2$CH$_3$); and 1.2 (t, 12H, CH$_3$). An elemental analysis yielded the following results in weight percent: C, 72.44; H, 6.00; N, 8.36, which compared with the following calculated values for C$_{60}$H$_{60}$N$_6$S$_2$O$_4$ in weight percent: C, 72.55; H, 6.09; N, 8.46.

Compound (7)

Compound (7) was obtained by a similar procedure for Compound (5) except that 2,5-dimercapto-1,3,4-thiadiazol (0.86 g, 5.73 mmol) replaced 4,4'-thiobisbenzenethiol (1.44 g, 5.73 mmol). The yield of Compound (7) was 4.4 g (77%). The $^1$H NMR spectrum (100 MHz) of the product in CDCl$_3$ was characterized by the following chemical shifts (δ, ppm): 8.9 (s, 2H, CH=N); 8.75 (m, 2H, Ar); 8.2–7.2 (m, 16H, Ar); 6.5 (d, 2H, 5-H of 1,2,4-subst. Ph); 6.2 (s, 2H, 3-H of 1,2,4-subst. Ph); 4.7–4.1 (m, 6H, OCH$_2$CH); 4.0–3.2 (m, 12H, SCH$_2$, OH, CH$_2$CH$_3$); and 1.25 (t, 12H, CH$_3$). An elemental analysis yielded the following results in weight percent: C, 66.94; H, 5.58; N, 10.96, which compared with the following calculated values for C$_{56}$H$_{56}$N$_8$S$_3$O$_4$ in weight percent: C, 67.17; H, 5.64; N, 11.19.

Compound (8)

Glycidyl ether of 4-diethylaminosalicylaldehyde 9-fluorenone azine (5.0 g, 11.8 mmol) and 2,2-bisphenylolpropane (1.28 g, 5.6 mmol, from Aldrich, Milwaukee, Wis.) were dissolved in 10 ml of 2-butanone. Triethylamine (0.65 ml, 4.7 mmol) was then added, and the mixture was refluxed for 15 hours. After the evaporation of the solvent, the residue was subjected to column chromatography (silica gel, grade 62, 60–200 mesh, 150 Å, Aldrich) using a mixture of acetone and hexane in a ratio of 1:4 by volume as the eluant. Fractions containing the product were collected, and the solvent was evaporated to from an oily residue. The oily residue was dissolved in toluene to form a 20 wt % solution, which was then poured with intensive stirring into a tenfold excess of n-hexane to yield 3.6 g (60%) of Compound (8). The $^1$H NMR spectrum (100 MHz) of the product in CDCl$_3$ was characterized by the following chemical shifts (δ, ppm): 8.9 (s, 2H, CH=N); 8.7 (m, 2H, Ar); 82–6.1 (m, 30H, Ar); 4.7–3.3 (m, 10H, CH$_2$CHCH$_2$); 3.5 (q, 4H, CH$_2$CH$_3$) 3.0 (m, 2H, OH); 1.65 (s, 6H, CH$_3$); and 1.3 (m, 12H, CH$_2$CH$_3$). An elemental analysis yielded the following results in weight percent: C, 76.40; H, 6.50; N, 7.77, which compared with the following calculated values for C$_{68}$H$_{70}$N$_6$O$_6$ in weight percent: C, 76.52; H, 6.61; N, 7.87.

2,7-Diamino-9-fluorenone 2,7-Dinitro-9-fluorenone (162 g, 0.6 mol, from Aldrich) was added cautiously to a solution of hydrated stannous chloride (1100 g, 4.9 mol, from Aldrich) in a mixture of concentrated hydrochloric acid (900 ml) and acetic acid (1600 ml). The suspension was stirred and refluxed for 1 hour. The mixture was cooled to room temperature, and a solid appeared. The solid was harvested by filtration. The solid was washed first with concentrated hydrochloric acid, and then with water until the filtrate color was violet. The residue was dissolved in boiling water. The solution was filtered and then made alkaline with sodium hydroxide to from a precipitate. The precipitate was washed with water, dried, and recrystallized from dioxane. The yield of 2,7-diamino-9-fluorenone was 108 g (85.7%). The melting point was found to be 284–286° C.

2,7-Bis(diethylamino)-9-fluorenone 2,7-Diamino-9-fluorenone (11.6 g, 0.055 mol) and iodoethane (50 g, 0.32 mol, from Aldrich Chemical) were dissolved in 150 ml of butanone, which was followed by the addition of 0.1 g of tetrabutylammonium iodide. The mixture was refluxed with a vigorous stirring. A 85% powdered KOH (21 g, 0.32 mol, obtained from Aldrich) was added in two portions during the reaction. After the reaction is completed, as determined by thin layer chromatography with a mixture of n-hexane and ethyl acetate in a ratio of 4:1 by volume as the eluant, the organic phase was separated. Then, the solvent and the excess iodoethane were evaporated off, and the residue was subjected to column chromatography (silica gel, grade 62, 60–200 mesh, 150 Å, Aldrich) using a mixture of ethyl acetate and n-hexane in a ratio of 1:10 by volume as the eluant. Fractions containing the product were collected, and the solvent was evaporated to yield 12.3 g (69%) of 2,7-bis(diethylamino)-9-fluorenone. The melting point was found to be 146.5–147.5° C. The $^1$H NMR spectrum (100 MHz) of the product in $CDCl_3$ was characterized by the following chemical shifts ($\delta$, ppm): 7.15 (s, 1H, Ar); 7.07 (s, 1H, Ar); 6.94 (d, J=2.6 Hz, 2H, Ar); 6.64 (d, J=2.7 Hz, 1H, Ar); 6.56 (d, J=2.6 Hz, 2H, $NH_2$); 3.35 (q, J=7.0 Hz, 8H, N($CH_2$$CH_3$)$_2$); and 1.16 (t, J=7.0 Hz, 12H, N($CH_2$$CH_3$)$_2$). An elemental analysis yielded the following results in weight percent: C, 78.19; H, 8.08; N, 8.52, which compared with the following calculated values for $C_{21}H_{26}N_2O$ in weight percent: C, 78.22; H, 8.13; N, 8.69.

2,7-Bis(diethylamino)-9-fluorenone hydrazone 2,7-Bis(diethylamino)-9-fluorenone (11.5 g, 35.66 mmol), 50 ml of 2-propanol, 98% hydrazine monohydrate (5.2 ml, 0.11 mol, from Aldrich), and 8 drops of concentrated hydrochloric acid (obtained from Aldrich) were added to a 100 ml 3-neck round bottom flask equipped with a reflux condenser and a mechanical stirrer. The mixture was refluxed with an intensive stirring until 2,7-bis(diethylamino)-9-fluorenone disappeared (1.5 hours). The reaction mixture was cooled to room temperature to form crystals. The crystals were filtered off, washed first with water, and then with a mixture of 2-propanol and n-hexane to yield 9.5 g (79%) of the hydrazone. The melting point was found to be 150–151° C. (recrystallized from 2-propanol). The $^1$H NMR spectrum (100 MHz) of the product in $CDCl_3$ was characterized by the following chemical shifts ($\delta$, ppm): 7.50–7.20 (m, 4H, Ar); 6.82–6.50 (m, 2H, Ar); 7.10 (s, br, 2H, $NH_2$); 7.00 (q, 8H, N($CH_2$$CH_3$)$_2$); and 3.75 (t, J=7.1 Hz, 12H, N($CH_2$$CH_3$)$_2$). An elemental analysis yielded the following results in weight percent: C, 74.69; H, 8.28; N, 16.52, which compared with the following calculated values for $C_{21}H_{28}N_4$ in weight percent: C, 74.96; H, 8.39; N, 16.65.

2,7-Bis(diethylamino)-9-fluorenone 4-Diethylamino-2-hydroxybenzaldehyde Azine 4-Diethylamino-2-hydroxybenzaldehyde (5.17 g, 26.75 mmol, from Aldrich) and 2,7-bis(diethylamino)-9-fluorenone hydrazone (9.0 g, 26.75 mmol) were refluxed in a mixture of 10 ml of 2-propanol and 5 ml of dioxane until one of the starting materials disappeared (3.5 hours). The solvents were evaporated, and the residue was dissolved in 2-propanol to form a solution. The solution was cooled to 5° C. to form crystals. The crystals were filtered off and washed with cold 2-propanol to yield 9.4 g (68.7%) of 2,7-bis (diethylamino)-9-fluorenone 4-diethylamino-2-hydroxybenzaldehyde azine. An elemental analysis yielded the following results in weight percent: C, 74.59; H, 7.68; N, 15.12, which compared with the following calculated values for $C_{32}H_{43}N_5O$ in weight percent: C, 74.82; H, 7.49; N, 15.03.

2,7-Bis(diethylamino)-9-fluorenone 4-Diethylamino-2-(1,2-epoxypropoxy)benzaldehyde azine A mixture of 2,7-bis(diethylamino)-9-fluorenone 4-diethylamino-2-hydroxybenzaldehyde azine (8.9 g, 16.35 mmol) and epichlorohydrin (20 ml, 0.25 mmol, commercially available from Aldrich) was stirred vigorously at 30–35° C. for 6 hours. During the reaction, powdered 85% potassium hydroxide (3.23 g, 0.05 mol) and anhydrous sodium sulfate (0.82 g, 6.54 mmol) were added in three portions with prior cooling of the reaction mixture to 20–25° C. After the termination of the reaction, the mixture was cooled to room temperature and filtered. The organic filtrate was added to ethyl acetate to form a solution. The solution was then washed with distilled water until the washed water was neutral. The solution was dried over anhydrous magnesium sulfate, treated with activated charcoal, and filtered. Then, the solvents were removed. The residue was subjected to column chromatography (silica gel, grade 62, 60–200 mesh, 150 Å, Aldrich) using a mixture of acetone and n-hexane in a ratio of 1:4 by volume as the eluant. Fractions containing the product were collected, and the solvents were evaporated to yield 5.8 g (59%) of 2,7-bis(diethylamino)-9-fluorenone 4-diethylamino-2,3-epoxypropylbenzaldehyde azine. The melting point was found to be 147–148.5° C. The $^1$H NMR spectrum (250 MHz) of the product in $CDCl_3$ was characterized by the following chemical shifts ($\delta$, ppm): 8.90 (s, 1H, CH=N); 8.32–8.05 (m, 2H, Ar); 7.40–7.12 (m, 3H, Ar); 6.82–6.50 (m, 2H, Ar); 6.32 (d, split, 1H, 5-H of 1,2,4-subst. Ph); 6.17 (s, split, 1H, 3-H, of 1,2,4-subst. Ph); 4.35 (m, 2H, NC$H_2$CH); 3.70–3.10 (m, 13H, CH, N(C$H_2$CH$_3$)$_2$; 3.05–2.85 (dd, 2H, one proton of OCH$_2$); 2.80–2.65 (dd, another proton of OCH$_2$); and 1.40–1.05 (m, 18H, N(CH$_2$C$H_3$)$_2$). An elemental analysis yielded the following results in weight percent: C, 73.99; H, 7.88; N, 12.21, which compared with the following calculated values for $C_{35}H_{45}N_5O_2$ in weight percent: C, 74.04; H, 7.99; N, 12.33.

Bis(4,4'-diethylamino)benzophenone hydrazone

Bis(4,4'-diethylamino)benzophenone (108.1 g, 0.335 mol, from Aldrich), 250 ml of 2-propanol, hydrazine monohydrate (98%, 244 ml, 5 mol, from Aldrich), and 10 ml of concentrated hydrochloric acid (from Aldrich) were added to a 1000 ml 3-neck round bottom flask equipped with a reflux condenser and a mechanical stirrer. The solution was refluxed with an intensive stirring until bis(4,4'-diethylamino)benzophenone disappeared (6 hours). The reaction mixture was allowed to stand overnight. The crystals that formed upon standing were removed by filtration and then washed with 2-propanol to yield 79.2 g (70%) of bis(4,4'-diethylamino)benzophenone hydrazone. The melting point was found to be 124–126° C. (recrystallized from 2-propanol). The $^1$H NMR spectrum (100 MHz) of the product in $CDCl_3$ was characterized by the following chemical shifts ($\delta$, ppm): 7.37 (d, J=9.0 Hz, 2H, Ar); 7.14 (d, J=8.8 Hz, 2H, Ar); 6.74 (d, J=8.8 Hz, 2H, Ar); 6.58 (d, J=9.0 Hz, 2H, Ar); 4.85 (s, br, 2H, NH$_2$); 3.36 (m, 8H, N(C$H_2$CH$_3$)$_2$; and 1.17 (m, 12H, N(CH$_2$C$H_3$)$_2$). An elemental analysis yielded the following results in weight percent: C, 74.49; H, 7.68; N, 15.12, which compared with the following calculated values for $C_{21}H_{30}N_4$ in weight percent: C, 74.52; H, 8.93; N, 16.55.

Bis(4,4'-diethylamino)benzophenone 4-Diethylamino-2-hydroxybenzaldehyde Azine 4-Diethylamino-2-hydroxybenzaldehyde (19.3 g, 0.1 mol, from Aldrich) and bis(4,4'-diethylamino)benzophenone hydrazone (28.2 g, 0.1 mol) were refluxed in 50 ml of dioxane until one of the starting materials disappeared (1 hour). The crystals that formed upon standing were filtered off and washed with 2-propanol and ether to yield 41 g (80%) of bis(4,4'-diethylamino)benzophenone 4-diethylamino-2-hydroxybenzaldehyde azine. The melting point was found to be 89.5–90.5° C. (recrystallized from dioxane). The $^1$H NMR spectrum (250 MHz) of the product in CDCl$_3$ was characterized by the following chemical shifts (δ, ppm): 11.91 (s, 1H, OH); 8.60 (s, 1H, CH═N); 7.59 (d, J=8.8 Hz; 2H, Ar); 7.24 (d, J=8.2 Hz, 2H, Ar); 7.07 (d, J=8.2 Hz, 1H, Ar); 6.85–6.50 (m, 4H, Ar); 6.40–6.10 (m, 2H, 3-H, 5-H of 1,2,4-subst. Ph); 3.55–3.15 (m, 12H, N(CH$_2$CH$_3$)$_2$); and 1.15 (m, 18H, N(CH$_2$CH$_3$)$_2$). An elemental analysis yielded the following results in weight percent: C, 74.59; H, 7.68; N, 15.12, which compared with the following calculated values for C$_{32}$H$_{43}$N$_5$O in weight percent: C, 74.82; H, 7.49; N, 15.03.

Compound (9)

Triethylamine (0.2 ml, 1.4 mmol, from Aldrich) was slowly added to a solution of 2,7-bis(diethylamino)-9-fluorenone 4-diethylamino-2-(1,2-epoxypropoxy)benzaldehyde azine (1.5 g, 2.64 mmol) and 4,4'-thiobisbenzenethiol (0.323 g, 1.29 mmol, from Aldrich) in 3 ml of 2-butanone while the temperature of the reaction mixture was maintained below 30° C. The reaction mixture was then stored over night at room temperature. After the evaporation of the solvent, the residue was subjected to column chromatography (silica gel, grade 62, 60–200 mesh, 150 Å, Aldrich) using a mixture of acetone and hexane in a ratio of 1:4 by volume as the eluant. Fractions containing the product were collected, and the solvent was evaporated to from an oily residue. The oily residue was dissolved in toluene to form a 20% solid solution, which was then poured with intensive stirring into a tenfold excess of n-hexane to yield 1.6 g (87%) of Compound (9). The $^1$H NMR spectrum (250 MHz) of the product in CDCl$_3$ was characterized by the following chemical shifts (δ, ppm): 8.77 (s, 2H, CH═N); 8.25–7.95 (m, 4H, Ar); 7.50–7.05 (m, 12H, Ar); 6.90–6.05 (m, 8H, Ar); 4.30–4.02 (m, 6H, OCH$_2$CH); 3.75–2.90 (m, 30H, CH$_2$S, OH, N(CH$_2$CH$_3$)$_2$); and 1.45–1.05 (m, 36H, N(CH$_2$CH$_3$)$_2$). An elemental analysis yielded the following results in weight percent: C, 72.96; H, 7.09; N, 10.07, which compared with the following calculated values for C$_{82}$H$_{100}$N$_{10}$S$_3$O$_4$ in weight percent: C, 71.06; H, 7.27; N, 10.11.

Compound (10)

Triethylamine (0.2 ml, 1.4 mmol) was slowly added to a solution of 2,7-bis(diethylamino)-9-fluorenone 4-diethylamino-2-(1,2-epoxypropoxy)benzaldehyde azine (1.5 g, 2.64 mmol) and 2,5-dimercapto-1,3,4-thiadiazole (0.20 g, 1.29 mmol) in 3 ml of 2-butanone, while the temperature of the reaction mixture was maintained below 30° C. The reaction mixture was stored over night at room temperature. After the evaporation of the solvent, the residue was subjected to column chromatography (silica gel, grade 62, 60–200 mesh, 150 Å, Aldrich) using a mixture of acetone and hexane in a ratio of 1:4 by volume as the eluant. Fractions containing the product were collected, and the solvent was evaporated to from an oily residue. The oily residue was dissolved in toluene to form a 20% solid solution, which was then poured with intensive stirring into a tenfold excess of n-hexane to yield 1.4 g (82%) of Compound (10). The $^1$H NMR spectrum (250 MHz) of the product in CDCl$_3$ was characterized by the following chemical shifts (δ, ppm): 8.77 (s, 2H, CH═N); 8.25–7.95 (m, 4H, Ar); 7.42–7.15 (m, 6H, Ar); 6.82–6.50 (m, 4H, Ar); 6.32 (d, split, 2H, 5-H of 1,2,4-subst. Ph); 6.12 (s, split, 1H, 3-H, of 1,2,4-subst. Ph); 4.45 (m, 2H, CH); 4.30–4.05 (m, 4H, OCH$_2$); 3.85–2.91 (m, 30H, CH$_2$S, OH, N(CH$_2$CH$_3$)$_2$); and 1.45–1.05 (m, 36H, N(CH$_2$CH$_3$)$_2$). An elemental analysis yielded the following results in weight percent: C, 67.06; H, 7.09; N, 12.97, which compared with the following calculated values for C$_{72}$H$_{92}$N$_{12}$S$_3$O$_4$ in weight percent: C, 67.26; H, 7.21; N, 13.07.

Compound (11)

Compound (11) may be prepared similarly according to the procedure for Compound (9) except that bis(4,4'-diethylamino)benzophenone 4-diethylamino-2-hydroxybenzaldehyde azine replaces 2,7-bis(diethylamino)-9-fluorenone 4-diethylamino-2-(1,2-epoxypropoxy)benzaldehyde azine.

Example 2

Charge Mobility Measurements

This example describes the measurement of charge mobility for charge transport materials comprising one of Compounds (2)–(5) and (7)–(10) as described above.

Sample 1

A mixture of 0.1 g of Compound (2) and 0.1 g of polyvinylbutyral (S-LEC B BX-1, from Sekisui Chemical, Japan) was dissolved in 2 ml of tetrahydrofuran. The solution was coated by the trough coating technique on a piece of polyester film coated with conductive aluminum layer. After the coating was dried for 1 hour at 80° C., a clear 100 μm thick layer was formed. The hole mobility of the sample was measured, and the results are presented in Table 1.

Sample 2

Sample 2 was prepared and tested similarly as Sample 1, except that Compound (3) replaced Compound (2).

Sample 3

Sample 3 was prepared and tested similarly as Sample 1, except that Compound (4) replaced Compound (2).

Sample 4

Sample 4 was prepared and tested similarly as Sample 1, except that Compound (5) replaced Compound (2).

Sample 5

Sample 5 was prepared and tested similarly as Sample 1, except that Compound (7) replaced Compound (2).

Sample 6

Sample 6 was prepared and tested similarly as Sample 1, except that Compound (8) replaced Compound (2).

Sample 7

A mixture of 0.1 g of the Compound (9) and 0.1 g of polycarbonate Z (PCZ-200, Mitsubishi Engineering Plastics Corp, White Plain, N.Y.) was dissolved in 2 ml of tetrahydrofuran. The solution was coated on a polyester film with conductive aluminum layer with a dip roller process. After the coating was dried for 1 hour at 80° C., a clear 10 μm thick layer was formed. The hole mobility of the sample was measured and the results are presented in Table 1.

Sample 8

Sample 8 was prepared and tested similarly as Sample 7, except that Compound (10) replaced Compound (9)

Mobility Measurements

Each sample was corona charged positively up to a surface potential U and illuminated with 2 ns long nitrogen laser light pulse. The hole mobility μ was determined as described in Kalade et al., "Investigation of charge carrier transfer in electrophotographic layers of chalkogenide glasses," Proceeding IPCS 1994: The Physics and Chemistry of Imaging Systems, Rochester, N.Y., pp. 747–752, incorporated herein by reference. The hole mobility measurement was repeated with changes to the charging regime to charge the sample to different U values, which corresponded to different electric field strength, E, inside the layer. This dependence on electric field strength was approximated by the formula $$\mu = \mu_0 e^{\alpha \sqrt{E}}.$$

Here, E is electric field strength, $\mu_0$ is the zero field mobility and $\alpha$ is Pool-Frenkel parameter. Table 1 lists the mobility characterizing parameters $\mu_0$ and $\alpha$ values and the mobility value at the $6.4 \times 10^5$ V/cm field strength as determined from these measurements.

working in the open input regime, for the photocurrent measurement. A $10^{-15}$–$10^{-12}$ amp photocurrent was flowing in the circuit under illumination. The photocurrent, I, was strongly dependent on the incident light photon energy hv. The $I^{0.5}$=f(hv) dependence was plotted. Usually, the dependence of the square root of photocurrent on incident light quanta energy is well described by linear relationship near the threshold (see references "Ionization Potential of Organic Pigment Film by Atmospheric Photoelectron Emission Analysis," *Electrophotography*, 28, Nr. 4, p. 364 (1989) by E. Miyamoto, Y. Yamaguchi, and M. Yokoyama; and "Photoemission in Solids," Topics in Applied Physics, 26, 1–103 (1978) by M. Cordona and L. Ley, both of which are incorporated herein by reference). The linear part of this dependence was extrapolated to the hv axis, and the Ip value was determined as the photon energy at the interception

TABLE 1

| Sample | $\mu_0$ (cm$^2$/V · S) | $\mu$ (cm$^2$/V · s) at $6.4 \cdot 10^5$ V/cm | $\alpha$ (cm/V)$^{0.5}$ | Ionization Potential (eV) |
|---|---|---|---|---|
| 1 [Compound (2)] | $1.3 \times 10^{-11}$ | $6 \times 10^{-9}$ | 0.0077 | 5.34 |
| 2 [Compound (3)] | $3 \times 10^{-13}$ | $8 \times 10^{-10}$ | 0.010 | 5.35 |
| 3 [Compound (4)] | $2 \times 10^{-12}$ | $1.3 \times 10^{-9}$ | 0.008 | 5.37 |
| 4 [Compound (5)] | $3 \times 10^{-11}$ | $1.2 \times 10^{-8}$ | 0.0074 | 5.35 |
| N/A [Compound (6)] | / | / | / | 5.35 |
| 5 [Compound (7)] | $4 \cdot 10^{-13}$ | $7 \cdot 10^{-10}$ | 0.0094 | 5.31 |
| 6 [Compound (8)] | $1 \cdot 10^{-13}$ | $4 \cdot 10^{-11}$ | 0.0074 | 5.40 |
| 7 [Compound (9)] | $2 \times 10^{-8}$ | $7 \times 10^{-7}$ | 0.0046 | 4.84 |
| 8 [Compound (10)] | $1 \times 10^{-7}$ | $3 \times 10^{-6}$ | 0.0042 | 4.80 |

Example 3

Ionization Potential Measurements

This example describes the measurement of the ionization potential for the charge transport materials comprising one of Compounds (2)–(10) described in Example 1.

To perform the ionization potential measurements, a thin layer of charge transport material about 0.5 µm thickness was coated from a solution of 2 mg of charge transport material in 0.2 ml of tetrahydrofuran on a 20 cm$^2$ substrate surface. The substrate was an aluminized polyester film coated with a 0.4 µm thick methylcellulose sub-layer.

Ionization potential was measured as described in Grigalevicius et al., "3,6-Di(N-diphenylamino)-9-phenylcarbazole and its methyl-substituted derivative as novel hole-transporting amorphous molecular materials," Synthetic Metals 128 (2002), p. 127–131, incorporated herein by reference. In particular, each sample was illuminated with monochromatic light from the quartz monochromator with a deuterium lamp source. The power of the incident light beam was 2–5·10$^{-8}$ W. A negative voltage of −300 V was supplied to the sample substrate. A counter-electrode with the 4.5×15 mm$^2$ slit for illumination was placed at 8 mm distance from the sample surface. The counter-electrode was connected to the input of a BK2-16 type electrometer, point. The ionization potential measurement has an error of ±0.03 eV. Table 1 lists the ionization potential value of Compounds (2)–(10).

As is well understood by those skilled in the art, additional substitution, variation among substituents, and alternative methods of synthesis and use may be practiced within the scope and intent of the present disclosure of the invention.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising:

(a) a charge transport material having the formula

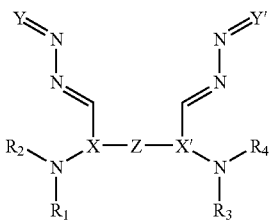

where $R_1$, $R_2$, $R_3$, and $R_4$ comprise, each independently, an alkyl group, an alkenyl group, an aromatic group, a heterocyclic group, or a part of a ring group;

X and X' comprise, each independently, an aromatic group;

Y and Y' comprise, each independently, a (disubstituted) methylene group; and

Z is a linking group;

(b) a charge generating compound; and (c) an electrically conductive substrate on which said charge transport material and said charge generating compound are located.

2. The organophotoreceptor of claim 1 further comprising a second charge transport material.

3. The organophotoreceptor of claim 2 wherein the second charge transport material comprises a charge transport compound.

4. The organophotoreceptor of claim 1 wherein X and X' are, each independently, a $C_6H_3$ group.

5. The organophotoreceptor of claim 1 wherein the (disubstituted)methylene group is selected form the group consisting of a 10H-anthracen-9-ylidene group, a 9-fluorenylidene group, and a diarylmethylene group.

6. The organophotoreceptor of claim 1 wherein the (disubstituted)methylene group is a (di-aromatic)methylene group.

7. The organophotoreceptor of claim 1 comprising:

(a) a charge transport layer comprising said charge transport material and a polymeric binder; and (b) a charge generating layer comprising said charge generating compound and a polymeric binder.

8. The organophotoreceptor of claim 1 wherein Z has the formula $-(CH_2)_m-$ where m is an integer between 1 and 20, inclusive, and one or more of the methylene groups is optionally replaced by O, S, C=O, O=S=O, a heterocyclic group, an aromatic group, urethane, urea, an ester group, an $NR_6$ group, or a $CR_8R_9$ group where $R_6$, $R_8$, and $R_9$ are, independently, H, hydroxyl, thiol, carboxyl, an amino group, an alkyl group, an alkenyl group, a heterocyclic group, or an aromatic group, or part of a ring group.

9. An electrophotographic imaging apparatus comprising:

(a) a light imaging component; and (b) an organophotoreceptor oriented to receive light from said light imaging component, said organophotoreceptor comprising:

(i) a charge transport material having the formula

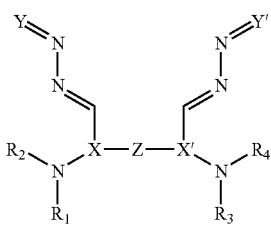

where $R_1$, $R_2$, $R_3$, and $R_4$ comprise, each independently, an alkyl group, an alkenyl group, an aromatic group, a heterocyclic group, or a part of a ring group;

X and X' comprise, each independently, an aromatic group;

Y and Y' comprise, each independently, a (disubstituted) methylene group; and

Z is a linking group;

(ii) a charge generating compound; and (iii) an electrically conductive substrate on which said charge transport material and said charge generating compound are located.

10. The electrophotographic imaging apparatus of claim 9 further comprising a toner dispenser.

11. The electrophotographic imaging apparatus of claim 9 wherein the organophotoreceptor further comprises a second charge transport material.

12. The electrophotographic imaging apparatus of claim 11 wherein said second charge transport material comprises a charge transport compound.

13. The electrophotographic imaging apparatus of claim 9 wherein the (disubstituted)methylene group is selected form the group consisting of a 10H-anthracen-9-ylidene group, a 9-fluorenylidene group, and a diarylmethylene group.

14. The electrophotographic imaging apparatus of claim 9 wherein the (disubstituted)methylene group is a (di-aromatic)methylene group.

15. The electrophotographic imaging apparatus of claim 9 wherein said organophotoreceptor comprises a belt or a drum that supports the electrically conductive substrate.

16. The electrophotographic imaging apparatus of claim 9 wherein X and X' are, each independently, a $C_6H_3$ group.

17. The electrophotographic imaging apparatus of claim 9 wherein Z has the formula $-(CH_2)_m-$ where m is an integer between 1 and 20, inclusive, and one or more of the methylene groups is optionally replaced by O, S, C=O, O=S=O, a heterocyclic group, an aromatic group, urethane, urea, an ester group, an $NR_6$ group, or a $CR_8R_9$ group where $R_6$, $R_8$, and $R_9$ are, independently, H, hydroxyl, thiol, carboxyl, an amino group, an alkyl group, an alkenyl group, a heterocyclic group, an aromatic group, or part of a ring group.

18. A charge transport material having the formula

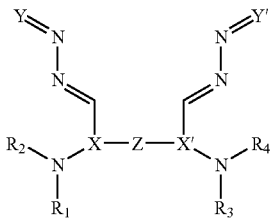

where $R_1$, $R_2$, $R_3$, and $R_4$ comprise, each independently, an alkyl group, an alkenyl group, an aromatic group, a heterocyclic group, or a part of a ring group;

X and X' comprise, each independently, an aromatic group;

Y and Y' comprise, each independently, a (disubstituted) methylene group; and

Z is a linking group.

19. The charge transport material of claim 18 wherein X and X' are, each independently, a $C_6H_3$ group.

20. The charge transport material of claim 18 wherein the (disubstituted)methylene group is selected form the group consisting of a 10H-anthracen-9-ylidene group, a 9-fluorenylidene group, and a diarylmethylene group.

21. The charge transport material of claim 18 wherein Z has the formula —$(CH_2)_m$— where m is an integer between 1 and 20, inclusive, and one or more of the methylene groups is optionally replaced by O, S, C=O, O=S=O, a heterocyclic group, an aromatic group, urethane, urea, an ester group, an $NR_6$ group, or a $CR_8R_9$ group where $R_6$, $R_8$, and $R_9$ are, independently, H, hydroxyl, thiol, carboxyl, an amino group, an alkyl group, an alkenyl group, a heterocyclic group, an aromatic group, or part of a ring group.

* * * * *